US012758520B2

(12) United States Patent
Ben-Sasson

(10) Patent No.: US 12,758,520 B2
(45) Date of Patent: Oct. 13, 2026

(54) GLYCERYLTRIACETATE (GTA) FOR USE IN IMPROVING BREATHING

(71) Applicant: YISSUM RESEARCH DEVELOPMENT COMPANY OF THE HEBREW UNIVERSITY OF JERUSALEM LTD., Jerusalem (IL)

(72) Inventor: Shmuel Ben-Sasson, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 914 days.

(21) Appl. No.: 17/997,840

(22) PCT Filed: May 3, 2021

(86) PCT No.: PCT/IL2021/050505

§ 371 (c)(1),
(2) Date: Nov. 3, 2022

(87) PCT Pub. No.: WO2021/224912

PCT Pub. Date: Nov. 11, 2021

(65) Prior Publication Data

US 2023/0338322 A1 Oct. 26, 2023

Related U.S. Application Data

(60) Provisional application No. 63/019,538, filed on May 4, 2020.

(51) Int. Cl.

| | |
|---|---|
| ***A61K 31/225*** | (2006.01) |
| ***A61K 9/48*** | (2006.01) |
| ***A61K 31/216*** | (2006.01) |
| ***A61P 11/00*** | (2006.01) |

(52) U.S. Cl.

CPC .......... *A61K 31/225* (2013.01); *A61K 9/4825* (2013.01); *A61K 31/216* (2013.01); *A61P 11/00* (2018.01)

(58) Field of Classification Search

CPC .................................................... A61K 31/225

See application file for complete search history.

(56) References Cited

U.S. PATENT DOCUMENTS

| | | | | |
|---|---|---|---|---|
| 3,966,962 | A | 6/1976 | Yalkowsky | |
| 10,765,654 | B2 * | 9/2020 | Jaworski | A61K 31/175 |
| 2013/0266643 | A1 * | 10/2013 | Moffett | A61K 31/225 424/490 |

FOREIGN PATENT DOCUMENTS

| | | | |
|---|---|---|---|
| CN | 104306908 | A | 1/2015 |
| CN | 111000801 | A | 4/2020 |
| WO | 13/013061 | A1 | 1/2013 |

OTHER PUBLICATIONS

Livan Delgado-Roche et al., Oxidative Stress as Key Player in Severe Acute Respiratory Syndrome Coronavirus (SARS-CoV) Infection, Arch Med Res. Apr. 30, 2020;51(5):384-387.*

Madhavarao et al., "Glyceryl triacetate for Canavan disease: A low-dose trial in infants and evaluation of a higher dose for toxicity in the tremor rat model", J Inherit Metab Dis (2009) 32:640-650.

Segel et al., "A safety trial of high dose glyceryl triacetate for Canavan disease", Molecular Genetics and Metabolism, (2011) vol. 103, Issue 3: 203-206.

Stolarz et al., "Fenofibrate Attenuates Neutrophilic Inflammation in Airway Epithelia: Potential Drug Repurposing for Cystic Fibrosis", Clin Trans Sci (2015) 8: 696-701.

Elaidy et al., "Modulation of the IL-23/IL-17 axis by fenofibrate ameliorates the ovalbumin/lipopolysaccharide-induced airway inflammation and bronchial asthma in rats", Naunyn-Schmiedeberg's Archives of Pharmacology (2018) 391: 309-321.

Fiume, "Final Report on the Safety Assessment of Triacetin", International Journal of Toxicology, vol. 22: 1-10, 2003.

* cited by examiner

*Primary Examiner* — Svetlana M Ivanova

(74) *Attorney, Agent, or Firm* — GREENBERG TRAURIG, LLP

(57) ABSTRACT

The present disclosure relates to glyceryltriacetate (GTA) compound for use in improving breathing in a subject experiencing a breathing difficulty. Of particular interest is the use of GTA for treating reduced lung function, such as that caused by lung infection and/or lung inflammation. Also disclosed is thus a composition and method for improving breathing of a subject experiencing a breathing difficulty.

18 Claims, No Drawings

GLYCERYLTRIACETATE (GTA) FOR USE IN IMPROVING BREATHING

RELATED APPLICATIONS

This application is U.S. National Phase patent application of International Application No. PCT/IL2021/050505, filed May 3, 2021, which claims the benefit of U.S. Provisional Application No. 63/019,538, filed May 4, 2020. Each of the aforementioned applications are incorporated herein by reference in its entirety for all purposes.

TECHNOLOGICAL FIELD

The present disclosure relates to uses of glyceryltriacetate (GTA).

BACKGROUND ART

References considered to be relevant as background to the presently disclosed subject matter are listed below:

International patent application publication No. WO13013061.

Madhavarao C. et al. *Inherit Metab Dis* (2009) 32:640-650

Segel R. et al. *Mol Genet Metab* (2011) 103:203-206

Acknowledgement of the above references herein is not to be inferred as meaning that these are in any way relevant to the patentability of the presently disclosed subject matter.

BACKGROUND

The potential application of GTA as a medication was already suggested beforehand in the context of Canavan disease (Madhavarao C. et al. (2009) and Segel R. et al. (2011)). It is noteworthy that the clinical trials of GTA for Canavan disease treatment failed to show any therapeutic benefit.

Similarly, a close look at the in-vivo tumor-model studies, presented as Examples in WO13013061, shows that an improvement was achieved only in combination with chemotherapy (TMZ) but not by GTA by itself. Indeed, GTA never reached a clinical trial stage for cancer treatment (Clinicaltrials.gov search, as of 13.04.2020).

GENERAL DESCRIPTION

The present disclosure provides, in accordance with a first of its aspects, a glyceryltriacetate (GTA) compound for use in a method of improving breathing of a subject experiencing a breathing difficulty.

Also disclosed herein is a method of improving breathing of a subject experiencing a breathing difficulty, said method comprises daily administering of a GTA compound in an amount that is effective to improve breathing in said subject.

In accordance with another aspect, the present disclosure provides a composition comprising as active ingredient GTA in an amount effective to improve breathing of a subject in need thereof.

Finally, provided by the present disclosure is a package comprising a composition comprising glyceryltriacetate (GTA) and instructions for use of the composition for improving breathing of a subject experiencing a breathing difficulty.

DETAILED DESCRIPTION OF EMBODIMENTS

The present disclosure is based on the finding that glyceryltriacetate (GTA) was effective in improving breathing in a subject that had breathing difficulties as a result of a lung disease that led to a reduced lung function in the subject. Based on this finding, it has been concluded that GTA can be utilized as a beneficial active ingredient in compositions for improving breathing in subjects that have, for example, a reduced lung function.

Glyceryltriacetate, which is an FDA-approved food additive, also known by any of the names triglyceride 1,2,3,-triacetoxypropate or in short, triacetin, is a compound having the molecular formula $(CH_3COOCH_2)_2CHOCOCH_3$ and has the following structure:

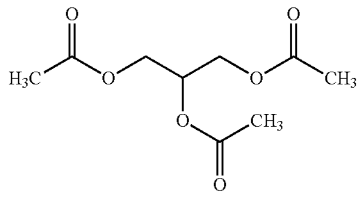

In the context of the present disclosure, the GTA is one having a purity grade that permits its use as a dietary supplement or a higher purity grade enabling its use in pharmaceutical compositions.

Without being bound by theory, it is assumed that administration of GTA at high doses is effective to increase acetate blood level and tissue bioavailability and thereby enhance the subject's acetylation capability and overcome conditions that are associated with local acetate or acetyl-CoA deficiency, and that may benefit from an augmentation of the acetylation powder.

The pathology of SARS-Coronaviruses family (SARS stands for Severe Acute Respiratory Syndrome), to which COVID-19 belongs, is typified by an increase in vascular permeability (de Wit E. et al. *Nat Rev Microbiol.* (2016) 14:523-34). In specific relation to the present disclosure, it was shown that enhancement of the acetylation-power of the cell via deacctylation-inhibition, prevents lung endothelial cell barrier disruption (Yu J. et al. *Am J Physiol Lung Cell Mol Physiol.* (2016) 311: L39-47). Likewise, such deacetylation-inhibitors prevent pulmonary endothelial hyperpermeability and acute lung injury by acetylation-dependent stabilization of microtubules and adherends junctions (Joshi A D. et al. *Am J Physiol Lung Cell Mol Physiol.* (2015) 309: L1410-9).

Without being bound by theory, the use of GTA at a dosage form comprising at minimum 1 gram GTA/day is believe to enrich the blood stream with acetate and enable cells to compensate for local deficiency. Normal circulating level of free acetate is relatively low, ~50 μM (Mueller N. et al. *Am J Clin Nutr* (2020) 111:545-54) and when 1 g GTA is hydrolyzed and spread in 10 L blood volume, it can increase acetate concentration by up to more than 20 folds. Cells can readily import acetate from the blood stream, which, in turn, will convert intracellularly to Acetyl-CoA by the enzyme ACSS2.

Therefore, the present disclosure provides a GTA compound for use in improving breathing of a subject, a composition comprising a GTA compound for improving breathing of a subject and a method for improving breathing of a subject, when the subject is experiencing a breathing difficulty, the GTA compound is used in an amount effective to improve breathing in said subject.

Also provided herein is a package comprising the composition of GTA and optionally instructions for use of the composition, for improving breathing in subjects having breathing difficulties.

For simplicity, the following description equally refers to the GTA compound, the composition comprising the GTA compound, the method or package of the present disclosure. As such, any description or definition relating to the compound for use or composition should be equally referred to as a description or definition of the method of package, mutatis mutandis, even if not explicitly stated so; and similarly any description of the method (or package) should be equally referred to as a description or definition of the compound for use or composition, mutatis mutandis.

The GTA used and formulated in an amount effective to achieve improvement in breathing. In some examples, the amount is at least 1 g per day. In some examples, the amount is any amount between 1 and 40 g a day. In some examples, the amount is any one of 1 g/day, 2 g/day, 3 g/day, 4 g/day, 5 g/day, 6 g/day, 7 g/day, 8 g/day, 9 g/day, 10 g/day, 11 g/day, 12 g/day, 13 g/day, 14 g/day, 15 g/day, 16 g/day, 17 g/day, 18 g/day, 19 g/day, 20 g/day, 21 g/day, 22 g/day, 23 g/day, 24 g/day, 25 g/day, 26 g/day, 27 g/day, 28 g/day, 29 g/day, 30 g/day, 31 g/day, 32 g/day, 33 g/day, 34 g/day, 35 g/day, 36 g/day, 37 g/day, 38 g/day, 39 g/day, 40 g/day or even more than 40 g/day.

The administration of GTA is for improving breathing in subjects experiencing breathing difficulties.

In the context of the present disclosure, the breathing difficulty and/or the improvement in breathing can be determined by self-assessment and/or by analytical tests, such as pulmonary function tests, as further discussed below.

In some examples, the breathing difficulty is associated or is a result of reduced lung function and can be characterized by any one of or any combination of shortness of breath, cough, typically dry cough, wheezing and gasping breath, amount of air inhaled or exhaled during normal breathing; total amount of air exhaled per minute; total volume of air that can be exhaled after inhaling as much as one can; amount of air left in lungs after exhaling normally; amount of air left in the lungs after exhaling as much as one can; total volume of the lungs when filled with as much air as possible; amount of air exhaled forcefully and quickly after inhaling as much as one can; amount of air expired during the first, second, and third seconds of the FVC test; average rate of flow during the middle half of the FVC test; fastest rate that one can force air out of his/her lungs. maximal pressure that can be produced by the patient trying to inhale through a blocked mouthpiece; single-breath diffusing capacity for carbon monoxide (DLCO); and oxygen saturation and desaturation at rest and during exercise.

In some examples, the improvement in breathing can be determined by self-assessment, e.g. improvement in at least one of the above symptoms, namely, shortness of breath, cough, typically dry cough, wheezing and gasping breath.

In additional or other examples, the reduced lung function and independently the improvement in breathing can be determined from measuring lung/pulmonary function parameters.

Thus, the improvement can be quantitative and/or qualitative.

In some examples, the pulmonary function parameter is determined using conventional pulmonary function tests (PFT), such as those performed using a spirometer or those performed using a plethysmography.

In some examples, the lung function parameters can be any one or combination of the following: Tidal volume (VT)—amount of air inhaled or exhaled during normal breathing; Minute volume (MV)—total amount of air exhaled per minute; Vital capacity (VC)—total volume of air that can be exhaled after inhaling as much as one can; Functional residual capacity (FRC)—amount of air left in lungs after exhaling normally; Residual volume—amount of air left in the lungs after exhaling as much as one can; Total lung capacity—total volume of the lungs when filled with as much air as possible; Forced vital capacity (FVC)—amount of air exhaled forcefully and quickly after inhaling as much as one can; Forced expiratory volume (FEV)—amount of air expired during the first, second, and third seconds of the FVC test; Forced expiratory flow (FEF)—average rate of flow during the middle half of the FVCtest; Peak expiratory flow rate (PEFR)—fastest rate that one can force air out of his/her lungs.

Additional or alternative parameters can be any one of maximal inspiratory pressure (MIP) being the maximal pressure that can be produced by the patient trying to inhale through a blocked mouthpiece; single-breath diffusing capacity for carbon monoxide (DLCO); and oxygen saturation-being the oxygen saturation and desaturation at rest and during exercise.

In some examples, the breathing difficulty is associated with a lung condition (lung discase or disorder).

In one example, the lung condition comprises at least viral infection.

In some examples, the viral infection is an infection caused by any one of coronaviruses, influenza viruses, respiratory syncytial viruses. In one preferred example, the viral infection is caused by coronavirus, preferably, but not exclusively, severe acute respiratory syndrome coronavirus 2 (Covid-19).

In one example, the lung condition comprises at least chronic obstructive pulmonary disease (COPD).

In one example, the lung condition comprises at least chronic bronchitis.

In one example, the lung condition comprises at least asthma.

In one example, the lung condition comprises at least bronchiectasis.

In one example, the lung condition comprises at least bronchiolitis.

In one example, the lung condition comprises at least cystic fibrosis.

In one example, the lung condition comprises at least pneumonia.

In one example, the lung condition comprises at least pneumoconiosis.

In one example, the lung condition comprises at least adult/acute respiratory distress syndrome (ARDS).

In one example, the lung condition comprises at least acute lung injury (ALI).

In one example, the lung condition comprises at least sepsis.

In one example, the lung condition comprises at least eosinophilic pneumonia.

In one example, the lung condition comprises at least tuberculosis.

In one example, the lung condition comprises at least sarcoidosis.

In one example, the lung condition comprises at least pulmonary fibrosis.

In one example, the lung condition comprises at least idiopathic pulmonary fibrosis.

In one example, the lung condition is a result of lobectomy.

In one example, the lung condition comprises at least lung cancer.

In one example, the lung condition comprises at least pneumonectomy.

In some examples, the composition comprising GTA and the method of its administration are for treating any one of the above lung conditions, namely, any one of lung viral infection, chronic obstructive pulmonary disease (COPD), chronic bronchitis, asthma, bronchiectasis, bronchiolitis, cystic fibrosis, pneumonia, pneumoconiosis, adult/acute respiratory distress syndrome (ARDS), acute lung injury (ALI), sepsis, eosinophilic pneumonia, tuberculosis, sarcoidosis, pulmonary fibrosis, idiopathic pulmonary fibrosis, lobectomy, lung cancer and pneumonectomy.

The GTA can be administered to the subject in need thereof by any ordinary route of administrating pharmaceutical compositions or may be administered as a food additive or dietary supplement.

In some examples, the GTA is formulated into a composition suitable for oral administration.

The compositions suitable for oral administration may be presented as discrete units, such as vials, capsules, tablets, lozenges, each containing at least 1 g GTA. Other compositions for oral administration can include suspensions in aqueous liquids or non-aqueous liquids such as a syrup, elixir, or an emulsion.

GTA is known to be bitter. Therefore, in some examples, particularly when administered orally, GTA can be combined with one or more beneficial additives that mask the bitter taste of GTA, such as sweeteners.

In some examples, GTA is formulated within a capsule. This includes soft gel capsules as well as hard gel capsules.

In some examples, the composition is formulated as a soft gel capsules. Non-limiting examples of soft gel capsules include those having a shell made of any one or combination of gelatin, starch, carrageenan, hydroxypropyl methylcellulose (HPMC).

In some other examples, the composition is a syrup comprising GTA and a taste masking additive. In such case, the amount of the composition administered is such that the subject receives at least 1 g GTA per day.

In some examples, the oral composition is a dietary supplement. In the context of the present disclosure, a dietary supplement which is also recognized in the art by the term food supplement refers to a preparation that is intended to enrich a subject's diet with a nutrient, in the present case, GTA. Dietary supplements are taken orally.

In some other examples, GTA is formulated as an oral pharmaceutical composition, i.e. a pharmaceutical composition suitable for oral administration.

In some examples, the oral pharmaceutical composition comprising GTA is formulated as an emulsion. The emulsion can be directly administered to the stomach by gavage.

An additional mode of administration that can be used include, without being limited thereto, injection. In some examples, the GTA for use, as disclosed herein, is formulated in a form suitable for intravenous injection. In this case, the composition can be, for example, in a form of an emulsion comprising the GTA and another liquid carrier forming together a composition suitable for infusion.

In some examples, the composition is in a form of oil in water (O/W) emulsion, similar to the well-known Intralipid emulsion. An O/W emulsion or fat emulsion for injection, such as Intralipid, refers to an emulsion of lipid for human intravenous use. Typical O/W emulsion comprise one of or a combination of triglycerides, such as soy bean oil, egg phospholipid and glycerin at different concentrations (e.g. 10%, 20%, 30%), although the present disclosure should not be limited to these specific combinations and when referring to an O/W, it should be understood as encompassing other lipids/fat combinations, optionally with other non-fat components such as amino acids, dextrose etc.

The composition disclosed herein can comprise an O/W emulsion in combination with the triglyceride GTA. In some examples, the composition for intravenous injection comprises a combination of at least one of GTA, soy bean oil, egg phospholipid and glycerin. In some examples, the composition comprises an O/W emulsion in combination with GTA, the latter at concentrations between 5% to 20%.

Yet additional mode of administration that can be used include, without being limited thereto, inhalation or insufflation. In some examples, the GTA for use, as disclosed herein, is formulated in a form suitable for a medical device used for delivering medication into the lungs by inhalation or insufflation. In this case, the composition can be, for example, in a form of an aqueous solution comprising the GTA at a concentration that typically will not exceed 0.25% (water solubility limit of GTA), and another liquid carrier forming together a composition suitable for inhalation. It is noted that this amount of GTA in water will provide about 30 mM of acetate equivalent, and thereby generate a local high concentration thereof. The delivery by inhalation can be, for example, in the form of an aerosol spray presented, e.g. in pressurized packs or nebulizer.

In some examples, irrespective of its mode of administration (e.g. dietary supplement, drug, oral, injection, inhalation etc.,), the composition comprises one or more additional beneficial agents (drug and/or dietary supplement).

In some examples, the additional beneficial agent is another dietary supplement.

In some examples, the additional beneficial agent is a therapeutically agent.

In some examples, the additional beneficial agent is one known to be effective in improving breathing.

In some other examples, the additional beneficial agent does not have a direct effect on breathing but when administered in combination with GTA, will increase the effect obtained by GTA alone on breathing.

In yet some other examples, the additional beneficial agent has an improving effect on lung functionality.

In some examples, the additional beneficial agent has an anti-viral effect.

In some other examples, the additional beneficial agent has an anti-inflammatory effect.

In yet some other examples, the additional beneficial agent has an immunomodulating effect, e.g. in stimulating or boosting the immune system.

At times, when GTA is combined with an additional beneficial agent, each can be in an amount that is less than the amount effective to improve breathing when GTA and/or said additional beneficial agent is administered as a sole active agent (in the same mode of administration). In some cases, such combined effect can be considered an adjuvant effect of the GTA on the additional beneficial agent or even a synergistic effect.

GTA or the composition comprising GTA, as disclosed herein, can be administered once or several times a day. When administered several time a day, the composition can comprise less than 1 g as long as the total daily amount is at least 1 g.

In some examples, the GTA or the composition comprising GTA, is administered on a daily basis, i.e. the method of treatment comprises daily administration of the disclosed composition for a period of two or more days.

In some examples, GTA or the composition comprising GTA, is administered every day until there is an improvement in at least the breathing of the subject receiving the composition.

In some examples, GTA or the composition comprising GTA is administered on a daily basis until at least one lung function parameter is considered to be improved according to a pre-determined standard/threshold and/or according to the physicians discretion to determine that there is a desired improvement.

DETAILED DESCRIPTION OF NON-LIMITING EXAMPLES

Example 1—Preparation of Soft-Gel Comprising Pure Glyceryl-Triacetate

Preparing Gelatin Ingredients

Gelatin (about 45% weight per weight of water) and glycerin (0.3-1.8% weight) are heated in a gelatin melting and mixing tank to uniformly mix and obtain a molten mass of liquid. Note that glycerin can be replaced or used in combination with sorbitol, both used as plasticizers. The heating temperature depends on the type of machine used.

The molten liquid is maintained hot in a liquid state to allow the gelatin molten to flow to a spreader box where the gelatin is spread and then cooled in a cooling drum to form a thin gelatin ribbon (ribbon shells, thickness determined, inter alia, by manner of operating the spreader box).

Preparing Fill Material

The fill material is pure glyceryl triacetate (GTA).

Encapsulation Process

The filling material is placed in a hopper and moved to the hot injection wedge where it injects the fill material through the die cavities of the tooling system. Simultaneously, two gelatin ribbons (from left and right) move into the tooling system. A die roller system cuts and seals hermetically the two ribbons together, with the fill material.

The resulting softgel capsules are dried to remove excess moisture. Drying is performed in a tumble dryer and placed on stackable trays for further room drying or drying within drying air tunnels.

The dried softgel capsules are then optionally sorted and polished.

Example 2—Treating Patient with Breathing Difficulties

A 92 old male diagnosed with lung cancer (NSCLC) at advanced stage, was suffering from shortness of breath, he looked pale and could not walk more than ~50 m without stopping for a rest. He did not receive any chemotherapy at that time and inhaled Salbutamol to ease his breathing. The patient started taking pure glyceryl-triacetate (GTA), encapsulated in hard-shell Vegicaps (produced by Capsugel), 12 ml a day, divided among 3 meals. After 3 days the patient increased the dose to 24 ml a day and after additional 3 days he consumed a daily dose of 30 ml GTA for a period of 1 month. Within 2 days after he started taking GTA, the patient reported that he feels much better and felt breathing is much easier. Within a week he stopped taking Salbutamol, was not pale anymore and started walking along hundreds of meters, without taking a break. This improvement was notwithstanding his CT, showing no improvement in tumor mass. The patient's oncological conditions did not improve and was therefore put on anti-cancer treatment without the GTA treatment and 1 month later passed away.

Example 3—Treating a SARS-Cov Infected Patient (COVID-19 Infection)

Subjects diagnosed with COVID-19 infection will be administered orally with softgel or hard capsules filled with GTA at a daily dose of up to 30 ml, either 4-10 ml three times a day or 6-15 ml twice a day, during or immediately after meal. Treatment duration will be for around 1-4 weeks and it is expected that the treatment will result in the acceleration of patient's healing, compared to non-treated patients having COVID-19 infection.

Example 4: Treating an Influenza-Virus Infected Patient (Swine-Flu Infection)

Subjects diagnosed with swine flu infection will be administered orally with softgel or hard capsules filled with GTA at a daily dose of up to 30 ml, either 4-10 ml three times a day or 6-15 ml twice a day, during or immediately after meal. Treatment duration will be for around 1-4 weeks and it is expected that the treatment will result in the acceleration of patient's healing, compared to non-treated patients having swine flu infection.

The invention claimed is:

1. A method of improving breathing of a subject suffering from a lung disease or disorder associated with reduced lung function that causes a breathing difficulty in the subject, said method comprising administering to the subject an amount of glyceryltriacetate (GTA), the amount being effective to improve breathing in the subject.

2. The method of claim 1, wherein said administration comprises administration of at least 1 g GTA a day.

3. The method of claim 1, wherein said reduced lung function is exhibited by any one or combination of shortness of breath, cough, wheezing, gasping breath, amount of air inhaled or exhaled during normal breathing; total amount of air exhaled per minute; total volume of air that can be exhaled after inhaling as much as one can; amount of air left in lungs after exhaling normally; amount of air left in the lungs after exhaling as much as one can; total volume of the lungs when filled with as much air as possible; amount of air exhaled forcefully and quickly after inhaling as much as one can; amount of air expired during first, second, and third seconds of a forced vital capacity (FVC) test; average rate of flow during the middle half of a FVC test; fastest rate that one can force air out of lungs, maximal pressure that can be produced by the patient trying to inhale through a blocked mouthpiece; single-breath diffusing capacity for carbon monoxide (DLCO); and oxygen saturation and desaturation at rest and during exercise.

4. The method of claim 1, wherein said reduced lung function is associated with any one or combination of restrictive lung disease, obstructive lung disease, lung comorbidity.

5. The method of claim 1, wherein said breathing difficulty is associated with a lung condition selected from lung inflammation or lung infection.

6. The method of claim 5, wherein said breathing difficulty is associated with a lung condition selected from the group consisting of lung viral infection, lung bacterial infection, chronic obstructive pulmonary disease (COPD), chronic bronchitis, asthma, pulmonary edema, bronchiectasis, bronchiolitis, cystic fibrosis, pneumonia, pneumoconiosis, adult/acute respiratory distress syndrome (ARDS), acute lung injury (ALI), sepsis, eosinophilic pneumonia, tuberculosis, sarcoidosis, pulmonary fibrosis, idiopathic pulmonary fibrosis, lobectomy, lung cancer and pneumonectomy.

7. The method of claim 6, wherein said lung viral infection is an infection caused by a Coronavirus.

8. The method of claim 1, comprising oral administration of said GTA.

9. The method of claim 1, comprising administration of said GTA in a form of a capsule.

10. The method of claim 9, wherein said capsule comprises at least 1 g GTA.

11. The method of claim 9, wherein said capsule comprises a shell composed of any one or combination of gelatin, starch, carrageenan, hydroxypropyl methylcellulose (HPMC).

12. The method of claim 1, wherein said GTA is administered in combination with at least one pharmaceutically acceptable agent.

13. The method of claim 12, wherein the at least one pharmaceutically acceptable agent is a therapeutically active agent and wherein said therapeutically active agent is one known to be effective in improving breathing and/or lung function.

14. The method of claim 13, wherein said therapeutically active agent is fenofibrate.

15. The method of claim 12, wherein said therapeutically active agent is in an amount that is less than the amount effective to improve breathing and/or lung function when said therapeutically active agent is administered as a sole therapeutically active agent.

16. The method according to claim 1, wherein said administration is in the form of a composition suitable for infusion.

17. The method of claim 1, wherein said administration is by inhalation or insufflation.

18. The method of claim 1, wherein said GTA is in a form of an aerosol comprising said GTA in an aqueous carrier.

* * * * *